(12) United States Patent
Sartawi

(10) Patent No.: US 9,931,213 B2
(45) Date of Patent: Apr. 3, 2018

(54) ACETABULAR CUP AND INSERTION HANDLE

(71) Applicant: Muthana Sartawi, Champaign, IL (US)

(72) Inventor: Muthana Sartawi, Champaign, IL (US)

( * ) Notice: Subject to any disclaimer, the term of this patent is extended or adjusted under 35 U.S.C. 154(b) by 0 days.

(21) Appl. No.: 15/251,196

(22) Filed: Aug. 30, 2016

(65) Prior Publication Data

US 2017/0065420 A1    Mar. 9, 2017

Related U.S. Application Data

(60) Provisional application No. 62/214,099, filed on Sep. 3, 2015.

(51) Int. Cl.
| | |
|---|---|
| *A61F 2/32* | (2006.01) |
| *A61F 2/34* | (2006.01) |
| *A61F 2/46* | (2006.01) |
| *A61F 2/30* | (2006.01) |

(52) U.S. Cl.
CPC .............. *A61F 2/34* (2013.01); *A61F 2/4609* (2013.01); *A61F 2/4684* (2013.01); *A61F 2002/30079* (2013.01); *A61F 2002/30131* (2013.01); *A61F 2002/3401* (2013.01); *A61F 2002/3432* (2013.01); *A61F 2002/4629* (2013.01); *A61F 2002/4677* (2013.01)

(58) Field of Classification Search
CPC ......... A61F 2/34; A61F 2/4604; A61F 2/4609
See application file for complete search history.

(56) References Cited

U.S. PATENT DOCUMENTS

| | | | |
|---|---|---|---|
| 5,725,591 A * | 3/1998 | DeCarlo, Jr. | ............. A61F 2/34 606/99 |
| 7,695,521 B2 | 4/2010 | Ely et al. | |
| 2007/0142921 A1* | 6/2007 | Lewis | .................... A61B 17/86 623/22.36 |

* cited by examiner

*Primary Examiner* — Brian Dukert
(74) *Attorney, Agent, or Firm* — Richard C Litman

(57) ABSTRACT

A hip joint apparatus is described. The apparatus has an acetabular cup designed for both seated engagement within a patient's acetabulum, and articulatory reception of a matingly shaped femoral component, wherein the dome of the acetabular cup has holes configured for accepting wires and variable angle locking screws to facilitate attachment of the acetabular cup to the acetabulum, and wherein the rim of the acetabular cup has holes configured for accepting wires to provide provisional stability to the acetabular cup. The apparatus also has an insertion handle with a graspable portion and a mating portion, the mating portion attached to the graspable portion and configured for engaging with the rim of the acetabular cup, thereby coupling the insertion handle to the acetabular cup.

10 Claims, 3 Drawing Sheets

ACETABULAR CUP AND INSERTION HANDLE

CROSS-REFERENCE TO RELATED PATENT APPLICATIONS

This application claims priority from Provisional U.S. Application 62/214,099, filed Sep. 3, 2015, titled "REVISION ACETABULAR COMPONENT," which is incorporated herein by reference in its entirety.

BRIEF DESCRIPTION OF THE DRAWINGS

Certain exemplary embodiments are described herein with reference to the following Figures, wherein.

DETAILED DESCRIPTION

The detailed description set forth below in connection with the appended drawings is intended as a description of various aspects of certain exemplary embodiments and is not intended to represent the only aspects of those embodiments. Each aspect described in this disclosure is provided merely as an example or illustration, and should not necessarily be construed as preferred or advantageous over other aspects. The detailed description includes specific details for providing an adequate understanding of the present disclosure. However, it will be apparent to those skilled in the art that the present disclosure may be practiced without these specific details. Acronyms and other descriptive terminology may be used merely for convenience and/or clarity and are not intended to limit the scope of the present disclosure. Any steps in a method should not be construed as needing to be carried out, or needing to be carried out in the order listed, unless stated otherwise.

Embodiments of the present disclosure relate generally to acetabular components. The exemplary embodiment relates to an acetabular cup and an offset insertion handle, which enable a surgeon to more effectively secure the acetabular cup inside a patient's acetabulum.

Hip surgery can be challenging when the patient has severe bone loss. In such cases, it can be a struggle for the surgeon to insert an acetabular cup and hold it in the appropriate position, while inserting screws to stabilize the cup for osseous integration. Accordingly, there exists a need to provide better ways to help the surgeon secure the acetabular cup in the acetabulum. To address this and/or other problems, the present disclosure includes, among other things, one or more exemplary systems, kits, methods, devices, assemblies, and/or components related to hip surgery. The exemplary embodiment uses K wire, variable angle locking screws, an offset insertion handle, and an acetabular cup design to aid in acetabular reconstruction.

Figure 1:
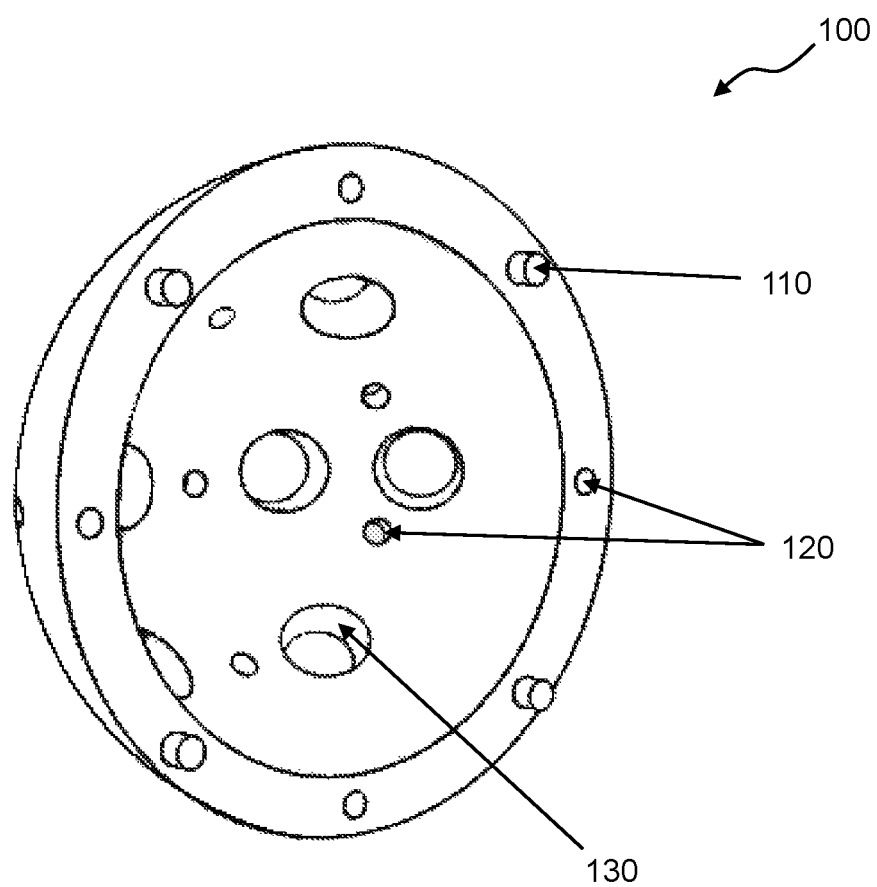
FIG. 1 is a front perspective view of an exemplary acetabular cup.

Referring to FIG. 1, a front perspective view of an exemplary acetabular cup 100 is shown. The acetabular cup 100 can have protrusions 110 located around its rim, wire holes 120 both on the rim and in the dome, and screw holes 130 in the dome. In the exemplary embodiment, the wire holes 120 are approximately 3.2 mm holes configured to accept K wire. In other embodiments, different types of wire and corresponding wire holes 120 may be used. The screw holes 130 are combination holes configured to accept different types of screws, such as cancellous screws and variable angle locking screws. The wire holes 120 can be used along with wire to provide provisional stabilization of the acetabular cup 100 in an appropriate position during surgery. The screw holes 130 can be used with a variety of different screws to secure the acetabular cup 100 to the acetabulum. The surgeon can choose which screws to place in which screw holes 130. For example, a cancellous screw can be placed in one screw hole 130 and a variable angle locking screw can be placed in another screw hole 130. In other embodiments, the number, arrangement, and size of the wire holes 120 and screw holes 130 can vary.

In one embodiment, the acetabular cup 100 uses cementless fixation and has a porous coating surface to allow osseous integration. In the exemplary embodiment, the acetabular cup 100 has properties to enable it to magnetically engage with an insertion handle.

Figure 2:
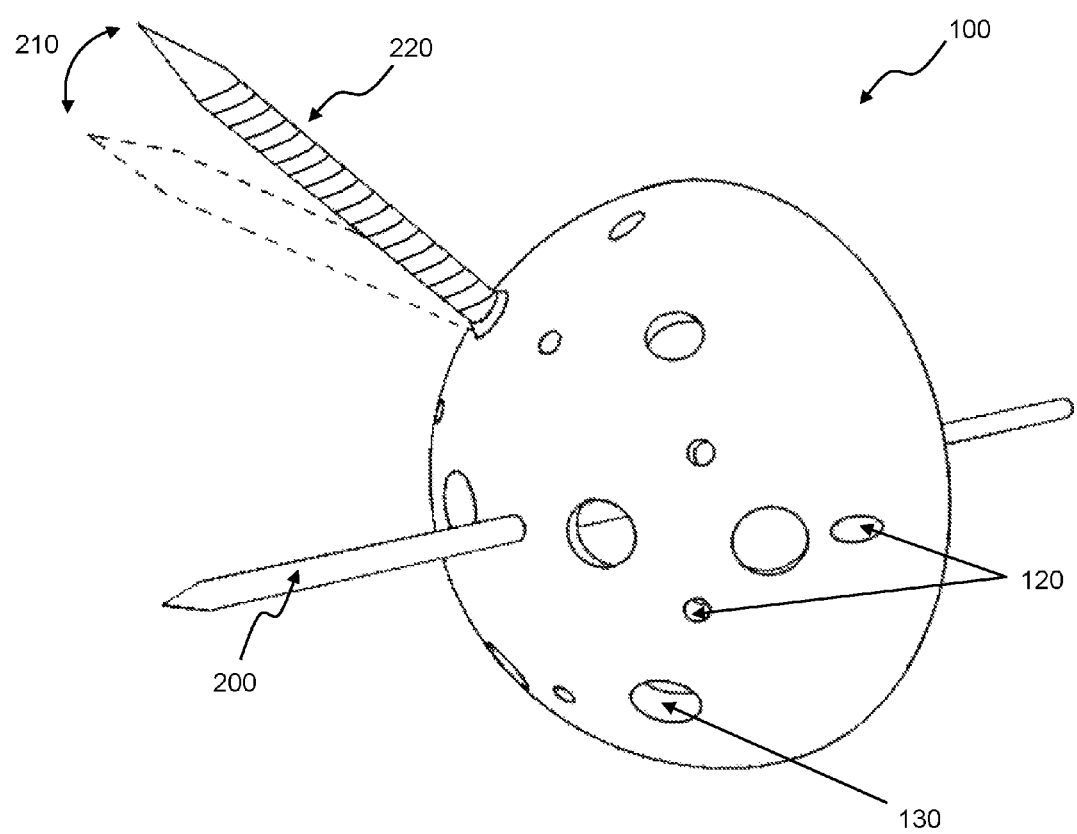
FIG. 2 is a back perspective view of the exemplary acetabular cup, depicted with exemplary securing means for assisting with securing the acetabular cup to an acetabulum.

Referring to FIG. 2, a back perspective view of the exemplary acetabular cup 100 is shown. In the exemplary embodiment, the acetabular cup 100 has a variable angle locking screw 220 threaded through one of the screw holes 130. The variable angle locking screw 220 can be angled through the screw hole 130 over an exemplary trajectory 210 of about 15 degrees. This allows the surgeon to secure the acetabular cup 100 to the acetabulum in a way that allows for more screw-bone purchase, accounting for locations in the acetabulum where bone loss may be more severe. The acetabular cup 100 also has a wire 200 inserted through the wire hole 120. The wire 200 can be used to provide provisional stability to the acetabular cup 100 while the surgeon inserts screws.

Figure 3A:
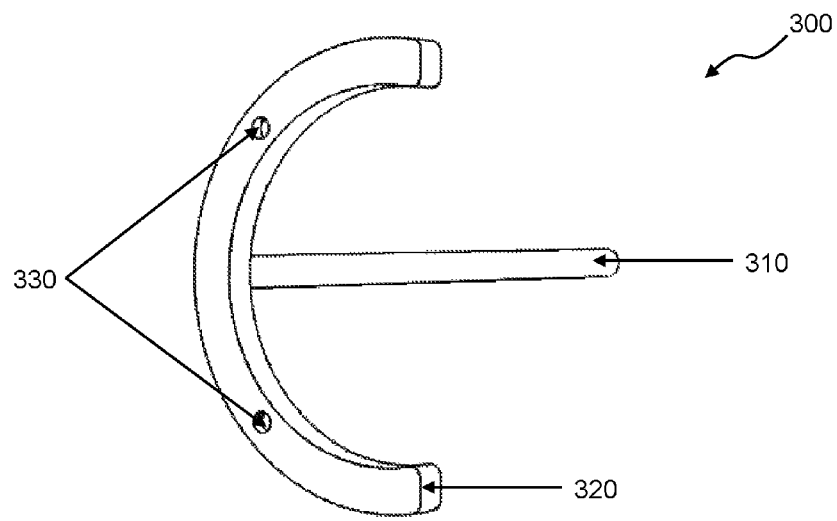
FIG. 3A is a perspective view of an exemplary insertion handle.

Referring to FIG. 3A, a perspective view of an exemplary insertion handle 300 is shown. The insertion handle 300 can have a graspable portion 310 and a mating portion 320. The mating portion 320 can have recesses 330 configured for engaging with the acetabular cup 100. In the exemplary embodiment, the mating portion 320 can align with at least a portion of the rim of the acetabular cup 100 (substantially covering at least a portion of the rim without substantially covering the generally part-spherical cavity of the lower side) and can be made of a magnetic material, thereby enabling a magnetic connection with the acetabular cup 100. This helps to prevent any torque forces on the acetabular cup 100 when the insertion handle 300 is detached. The magnet can be of a strength so as to not hurt any provisional stability upon removal, but strong enough, together with protrusions 110 and recesses 330, to hold and help position the acetabular cup 100 during surgery. The recesses 330 can correspond to the protrusions 110 of the acetabular cup 100, such that when the mating portion 320 engages with the acetabular cup 100, the protrusions 110 enter the recesses 330 and help secure the engagement. In the exemplary embodiment, the protrusions 110 and recesses 330 are spaced in such a way that they provide rotational stability to the acetabular cup 100 when the graspable portion 310 is being held and a screw is being threaded into a screw hole 130. However, if recesses 330 were, for example, located too closely together or too close to the longitudinal axis of the graspable portion 310, they might not provide adequate rotational stability.

In some embodiments, the number and location of the protrusions 110 and recesses 330 can be varied to achieve the desired effect. In some embodiments, the recesses can be located on the acetabular cup 100 instead, with the protrusions 110 being located on the mating portion 320.

In other embodiments, other means of coupling the insertion handle 300 with the acetabular cup 100 can be used. For example, the mating portion 320 of insertion handle 300 can essentially be an acetabular cup 100 template. The template can be a smaller version of the acetabular cup 100, with corresponding wire holes 120 and screw holes 130 to match those of acetabular cup 100. The mating portion 320, as a template of acetabular cup 100, can fit into the articulation surface of acetabular cup 100 while still enabling the surgeon to see and access the wire holes 120 and screw holes 130. This type of engagement of the insertion handle 300 can provide more surface area contact and therefore stability when inserting the acetabular cup 100 and screws into the acetabulum.

In another embodiment, the mating portion 320 can be a snap or clip fit mechanism to snap or clip onto the rim of acetabular cup 100. The acetabular cup 100 can have corresponding structure to enable a snap or clip fit of the mating portion 320 to its rim. In yet other embodiments, the mating portion 320 can be threaded and configured to screw into the rim of acetabular cup 100. The acetabular cup 100 can have corresponding structure to enable the mating portion 320 to be screwed into its rim. In some embodiments, the mating portion 320 can screw or clip into the center of acetabular cup 100, instead of or in addition to the rim.

Figure 3B:
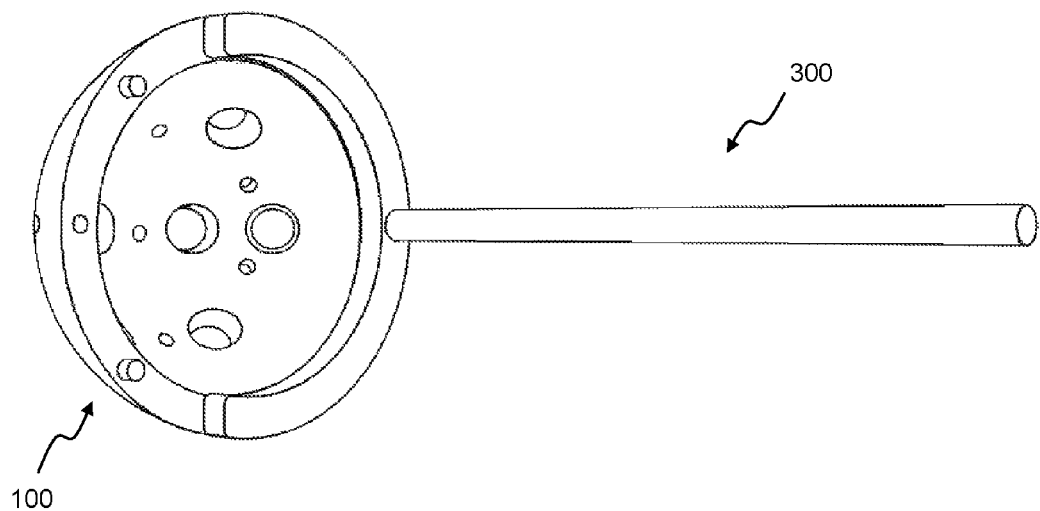
FIG. 3B is a perspective view of the exemplary insertion handle, coupled with the exemplary acetabular cup.

Referring to FIG. 3B, a perspective view of the exemplary insertion handle 300, coupled with the exemplary acetabular cup 100 is shown. The insertion handle 300 can be placed in various positions around the circumference of the acetabular cup 100. In the exemplary embodiment, based on the number and location of protrusions 110 and recesses 330, the insertion handle 300 can be engaged with the acetabular cup 100 on its right-hand, left-hand, top, or bottom sides. This allows the surgeon and/or their assistant to choose the best location for the insertion handle 300, so as to hold the acetabular cup 100 securely in place and to provide an unobstructed view and access of the acetabular cup 100 to the surgeon.

In the exemplary embodiment, the insertion handle 300 is an offset insertion handle, in that the graspable portion 310 ends up being located at the rim of the acetabular cup 100, rather than at its center. Additionally, the mating portion 320 uses magnetic means to engage with the acetabular cup 100, rather than threaded means. This reduces torque forces on the acetabular cup 100 when the insertion handle 300 is being detached, thereby improving pressfit stability of the acetabular cup 100 in the acetabulum. This can be important especially in cases of severe bone loss, where pressfit stability may be low. The use of the offset insertion handle 300, combined with the mating portion's 320 and acetabular cup's 100 magnetic properties, and the combination screw holes 130 and wire holes 120, can help with performing hip surgery, especially in cases with severe bone loss.

An exemplary technique is for the surgeon to first impact the acetabular cup 100 in place. The surgeon can use the offset insertion handle 300 to have easy access to the screw holes 130 and wire holes 120. The wire 200 can be used to provisionally hold the acetabular cup 100 if there is a poor press fit. The surgeon can then insert a cancellous screw to compress the acetabular cup 100 to the surrounding bone. This can then be followed by insertion of variable angle locking screws 220 and/or one or more cancellous or other screws, depending on the patient's bone quality and the intrinsic stability of the acetabular cup 100. The addition of variable angle locking screws 220 provides more stable fixation than standard non-locking screws, especially in cases with severe bone loss, osteoporotic bone, or when the acetabular cup 100 is not fully seated. The variable angle locking screws 220 can be angulated over trajectory 210 in all directions to achieve adequate screw-bone purchase. This can be most useful in revision scenarios with large bony defects. Once the screws are inserted and the surgeon is satisfied with stability of the acetabular cup 100, the wire 200 can be removed. A polyethylene liner can then be inserted into the articulation surface of the acetabular cup 100, and impacted into place. The femoral head can then be reduced into the acetabular cup 100.

Other objects and features of the present disclosure will become apparent as the description proceeds, especially when taken in conjunction with the accompanying drawing sheets illustrating embodiments of the disclosure.

What is claimed is:

1. A hip-joint apparatus comprising:
an acetabular cup defining a convex upper side having a size and shape adapted for seated engagement within a patient's acetabulum, and a lower side defining a downwardly open and generally part-spherical cavity lined by an articulation surface having a size and shape for articulatory reception of a matingly shaped femoral component, the acetabular cup further including a rim defined by a circumferential free edge between the upper and lower sides; and
an insertion handle consisting of a graspable portion and a mating portion, the mating portion attached to the graspable portion and configured for engaging with the rim of the acetabular cup, thereby coupling the insertion handle to the acetabular cup, wherein the mating portion of the insertion handle consists of recesses to accept at least two protrusions located on the rim of the acetabular cup, the recesses configured for assisting with the attachment of the insertion handle to the acetabular cup and providing rotational stability to the acetabular cup during surgery.

2. The apparatus according to claim 1, wherein the mating portion is comprised of a magnetic material and configured for enabling the insertion handle to attach and detach from the acetabular cup without significantly torqueing the acetabular cup.

3. The apparatus according to claim 1, wherein the mating portion covers at least a portion of the rim without covering the part-spherical cavity of the lower side.

4. The apparatus according to claim 1, wherein the acetabular cup includes a dome defined by the convex shape between the upper and lower sides, wherein the dome includes holes configured for accepting wires and variable angle locking screws to-facilitate attachment of the acetabular cup to the acetabulum.

5. The apparatus according to claim 1, wherein the rim includes holes configured for accepting wires.

6. A hip-joint apparatus comprising:
an acetabular cup defining a convex upper side having a size and shape adapted for seated engagement within a patient's acetabulum, and a lower side defining a downwardly open and generally part-spherical cavity lined by an articulation surface having a size and shape for articulatory reception of a matingly shaped femoral component, the acetabular cup further including a rim defined by a circumferential free edge between the upper and lower sides; and
an insertion handle comprising a graspable portion and a mating portion, the mating portion attached to the graspable portion and configured for engaging with the rim of the acetabular cup, thereby coupling the insertion handle to the acetabular cup, wherein the mating portion is comprised of a magnetic material and configured for enabling the insertion handle to magnetically attach and detach from the acetabular cup without significantly torqueing the acetabular cup.

7. The apparatus according to claim 6, wherein the acetabular cup includes a dome defined by the convex shape between the upper and lower sides, wherein the dome includes holes configured for accepting wires and variable angle locking screws to-facilitate attachment of the acetabular cup to the acetabulum.

8. The apparatus according to claim 6, wherein the rim includes holes configured for accepting wires.

9. The apparatus according to claim 6, wherein the mating portion covers at least a portion of the rim without covering the part-spherical cavity of the lower side.

10. A method for inserting an acetabular cup into a patient's acetabulum, comprising:
providing an acetabular cup, the acetabular cup defining a convex upper side having a size and shape adapted for seated engagement within a patient's acetabulum, and a lower side defining a downwardly open and generally part-spherical cavity lined by an articulation surface having a size and shape for articulatory reception of a matingly shaped femoral component, the acetabular cup having:
 a) a dome defined by the convex shape between the upper and lower sides, wherein the dome includes holes configured for accepting wires and variable angle locking screws to facilitate attachment of the acetabular cup to the acetabulum,
 b) a rim defined by the circumferential free edge between the upper and lower sides, wherein the rim includes holes configured for accepting wires;
providing an insertion handle, the insertion handle consisting of a graspable portion and a mating portion, the mating portion attached to the graspable portion and configured for engaging with the rim of the acetabular cup, thereby coupling the insertion handle to the acetabular cup, wherein the mating portion of the insertion handle consists of recesses to accept at least two protrusions located on the rim of the acetabular cup, the recesses configured for assisting with the attachment of the insertion handle to the acetabular cup and providing rotational stability to the acetabular cup during surgery;
coupling the acetabular cup with the insertion handle;
inserting the acetabular cup into the patient's acetabulum;
inserting a variable angle locking screw to secure the acetabular cup to the acetabulum; and
decoupling the insertion handle from the acetabular cup.

\* \* \* \* \*